United States Patent [19]
Morris

[11] Patent Number: 5,726,748
[45] Date of Patent: Mar. 10, 1998

[54] OPTICAL DISC CLOUD ANALYZER

[75] Inventor: William Guy Morris, Rexford, N.Y.

[73] Assignee: General Electric Company, Schenectady, N.Y.

[21] Appl. No.: 685,760

[22] Filed: Jul. 24, 1996

[51] Int. Cl.[6] ................................................ G01N 21/88
[52] U.S. Cl. .................................. 356/237; 356/430
[58] Field of Search ................................ 356/237, 430

[56] References Cited

U.S. PATENT DOCUMENTS

| | | | |
|---|---|---|---|
| 4,464,050 | 8/1984 | Kato et al. | 356/237 |
| 4,477,890 | 10/1984 | Mooney et al. | 369/53 |
| 4,848,864 | 7/1989 | Ostertag et al. | 350/6.8 |
| 4,954,723 | 9/1990 | Takahashi et al. | 250/572 |

FOREIGN PATENT DOCUMENTS 0152165  8/1985  European Pat. Off. .

*Primary Examiner*—Frank G. Font
*Assistant Examiner*—Zandra V. Smith
*Attorney, Agent, or Firm*—Ernest G. Cusick; William H. Pittman

[57] ABSTRACT

An analyzer is employed for detecting a cloud in an optical disc having a transparent surface layer atop a substrate and data pits therebetween. A light beam is projected at an acute incidence angle atop the surface layer to define a light spot covering a plurality of the pits. Light scattered from the pits below the spot is detected obliquely to both the incident light beam and a specular reflection thereof. The light spot is scanned over the surface layer, and variation of detected light intensities over the disc is determined for detecting a cloud. In a preferred embodiment, the scattered light is detected from two different oblique directions to increase contrast of the cloud.

28 Claims, 5 Drawing Sheets

OPTICAL DISC CLOUD ANALYZER

BACKGROUND OF THE INVENTION

The present invention relates generally to measuring quality of optical discs, and, more specifically, to detecting and measuring clouds therein.

Optical discs are available in various forms for recording audio, video, and/or computer data in significantly large amounts in a relatively small area. A typical optical disc includes a reflective substrate having a transparent surface layer, with data pits found therebetween. In a typical optical disc, commonly referred to as a compact disc (CD), a transparent polymer is injection molded and stamped to form the required data pits thereon. And, a reflective, metallized surface is suitably bonded to the transparent layer at the pits, thusly positioning the pits internally inside the optical disc.

The exposed surface of the transparent layer is smooth, and the data pits are conventionally read or decoded using a suitable light beam such as a laser which is projected perpendicularly to the surface layer for illuminating the individual pits in sequence. Light is reflected from the pits and suitably decoded in an electrical processor in a preferred form such as audio, video, or simply data.

A common defect found in optical discs is known as a "cloud" which appears as a hazy or slightly opaque region inside the transparent surface layer of the disc. One or more clouds may extend over varying area of the optical disc and may vary in contrast and extent. The clouds are aesthetically unpleasing and typically do not affect the quality or function of the disc. However, excessively severe clouds typically cause a disc to be rejected during the manufacturing process for failing to meet desired quality standards. The severity of clouds is typically rated by visual examination by quality control inspectors, and therefore the ratings may vary based on subjective interpretation by the different inspectors, as well as by the direction of the viewing light and angle of viewing.

More specifically, the specific cause of clouding is not fully understood and is not readily attributable to viewable discrete defects in the optical disc. Like a typical atmospheric cloud, an optical disc cloud is hazy in appearance and most likely due to very small defects introduced in the optical disc during manufacture. It is believed that clouds are formed by features smaller than the micron size pits found inside the transparent surface layer of the disc at the boundary with the internal data pits therein. Optical discs formed without data pits do not experience clouding, whereas optical discs formed with the data pits often do.

Complicating the ability to discern clouds in optical discs is the observation that the extent and severity of clouds changes as the direction of illumination or viewing changes. For example, a cloud which appears darker than the surrounding region can frequently be made to reverse contrast and appear lighter than the surrounding region by simply changing the direction of illumination or viewing. If an optical disc is not viewed in the right direction, then an objectionable cloud may be overlooked during the visual inspection thereof.

Accordingly, it is desired to provide a method and apparatus for automatically and accurately detecting clouds in an optical disc without the need for visual inspectors. And, it is also desirable to provide a single cloud rating or index indicating the degree of clouding in an individual disc so that it may be rejected or accepted during the quality control inspection thereof.

SUMMARY OF THE INVENTION

An analyzer is disclosed for detecting a cloud in an optical disc having a transparent surface layer atop a substrate and data pits therebetween. A light beam is projected at an acute incidence angle atop the surface layer to define a light spot covering a plurality of the pits. Light scattered from the pits below the spot is detected obliquely to both the incident light beam and a specular reflection thereof. The light spot is scanned over the surface layer, and variation of detected light intensities over the disc is determined for detecting a cloud. In a preferred embodiment, the scattered light is detected from two different oblique directions to increase contrast of the cloud.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION; PREFERRED EMBODIMENTS

Figure 1:
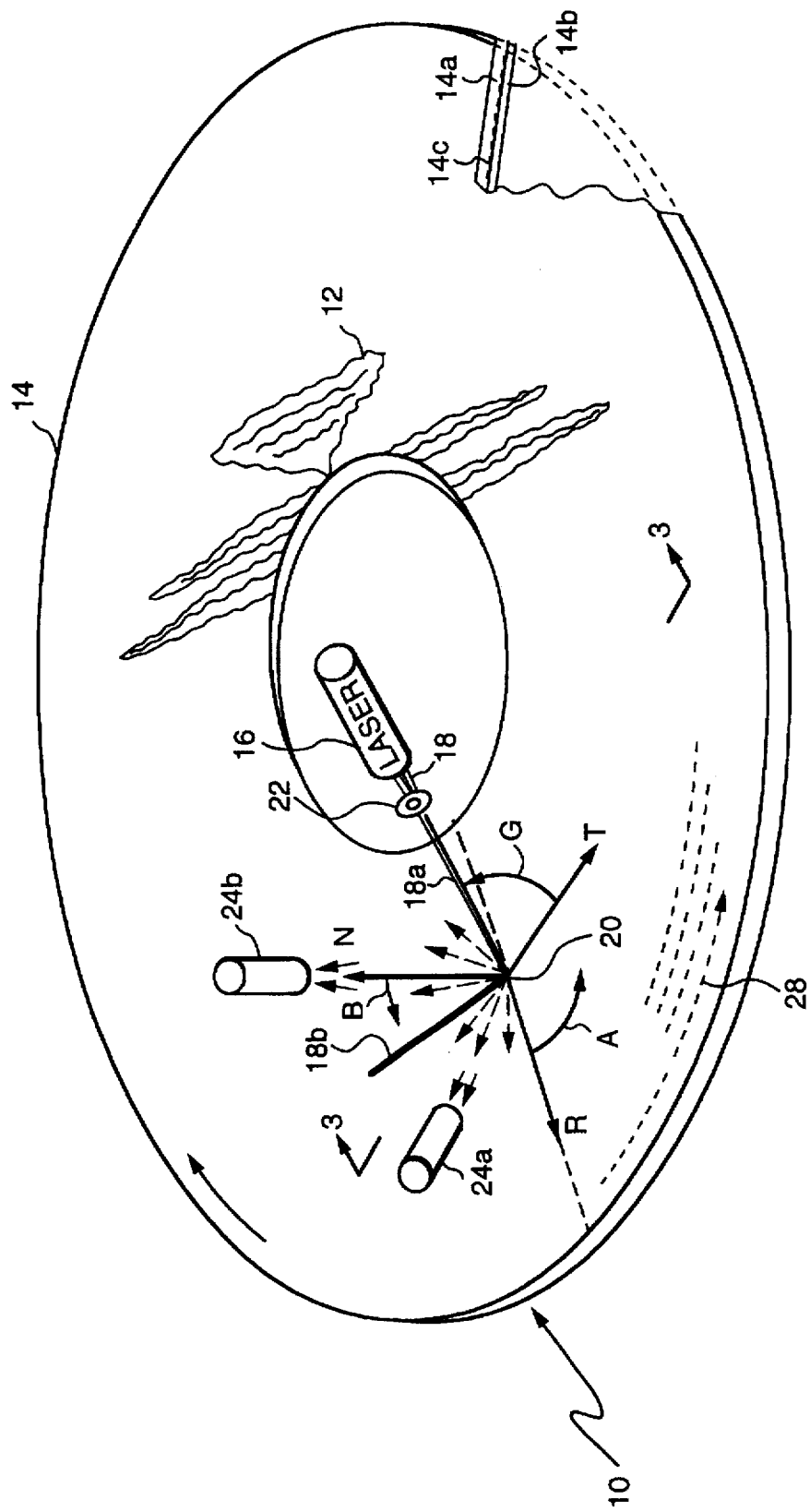
FIG. 1 is a schematic representation of a cloud analyzer in accordance with an exemplary embodiment of the present invention for detecting clouds in an optical disc.

Illustrated schematically in FIG. 1 is a cloud analyzer 10 in accordance with an exemplary embodiment for practicing a method of detecting a cloud 12 inside a conventional optical disc 14. The disc 14 may take any suitable form including, for example, that known as a compact disc (CD) typically made by injection molding a transparent polymer to provide a transparent surface layer 14a atop a metallized substrate 14b, with a suitable density of laterally spaced apart data pits 14c being disposed at the juncture therebetween inside or internal to the optical disc 14. The pits 14c are typically formed by stamping corresponding indentations into the lower surface of the transparent layer 14a, followed in turn by forming the metallized substrate 14b.

FIG. 1 illustrates schematically an exemplary form of the cloud 12, which may vary in form, area, and severity at one or more locations in the disc 14. As indicated in the background section, the cloud 12 is a common defect and appears to be generated by very small defects at the individual pits 14c themselves, with the pits 14c being very small to begin with. The pits 14c are conventionally read by projecting a scanning laser beam perpendicularly to the surface layer 14a and optically detecting the specular reflection thereof as the laser beam impinges individual ones of the pits 14c. Any clouds 12 in the disc 14 do not typically interfere with reading of the individual pits 14c, and are therefore undiscerned by the conventional disc reader.

In accordance with the present invention, means in the exemplary form of a conventional light projector or laser 16 are provided for projecting a collimated laser light beam 18 at an acute incidence angle G atop the surface layer 14a to define a light spot 20 covering a plurality of the pits 14c. In the exemplary embodiment illustrated in FIG. 1, a conventional aperture 22 is suitably optically aligned with the laser 16 for limiting or controlling the size of the spot 20 so that it preferably covers a plurality of the pits 14c, yet is smaller than the overall size of the cloud 12 being detected for discerning portions thereof without reading individual ones of the pits 14c themselves. The light projector or source 16 may be in the form of a conventional red laser diode having a 670 nm wavelength and an output power of 5 mw, with the aperture 22 being sized for producing a spot 20 on the disc surface of approximately 0.5 mm in diameter for covering thousands of pits 14c.

Means in the form of one or more conventional photodetectors 24a,b are provided for detecting intensity of light scattered from the pits 14c below the spot 20 obliquely to both the incident light beam designated 18a, and the specular reflection thereof designated 18b, as well as diffraction orders thereof. It is not desirable to detect either the incident or reflected beams 18a,b themselves since this would mask the cloud, but instead light scattered due to the small defects which create the cloud 12 is detected. Scattered light is different than specular reflection since it disperses in all directions above the disc 14, whereas the reflected specular beam 18b is reflected from the surface layer 14a at the same acute angle G as that of the incident beam 18a. Similarly, light reflected off of individual ones of the pits 14c specularly reflects at the same incidence angle of the light thereto. Such specular reflection light is not effective in discerning the cloud, whereas scattered light is effective for discerning the cloud 12.

Figure 2:
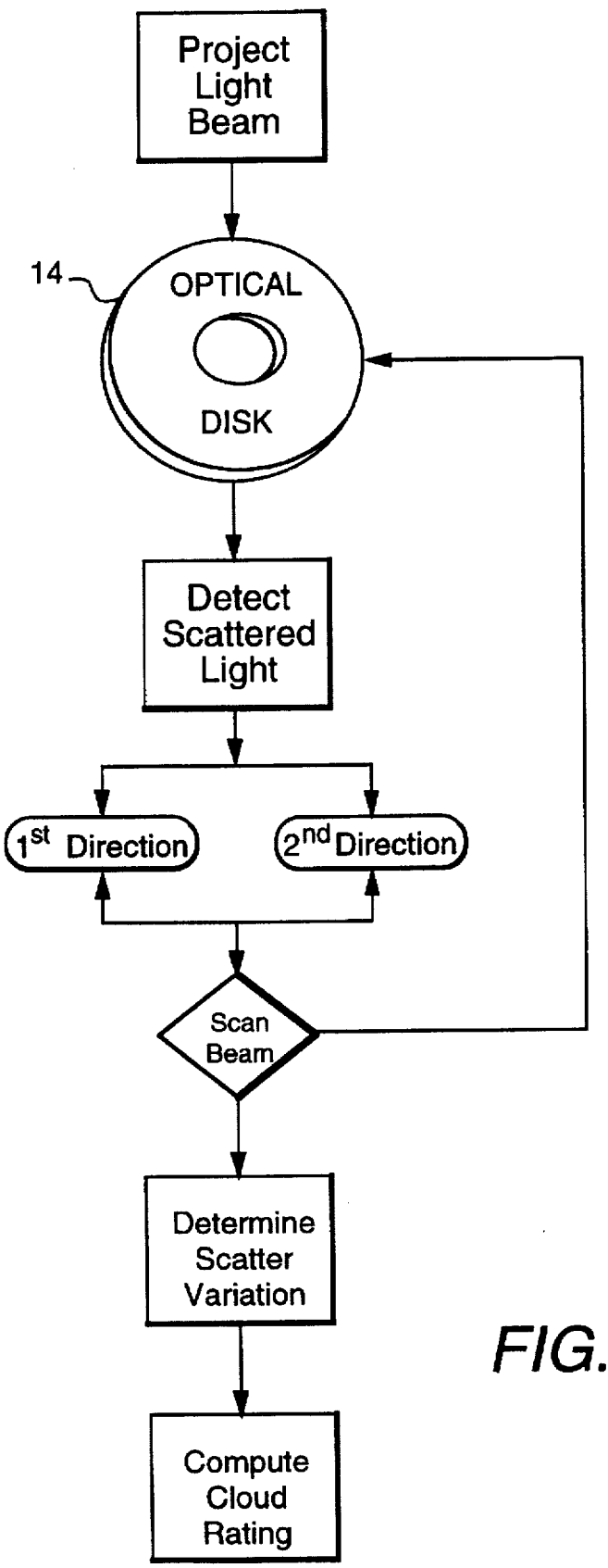
FIG. 2 is an exemplary flowchart representation of a method of detecting clouds in the optical disc illustrated in FIG. 1.
Figure 3:
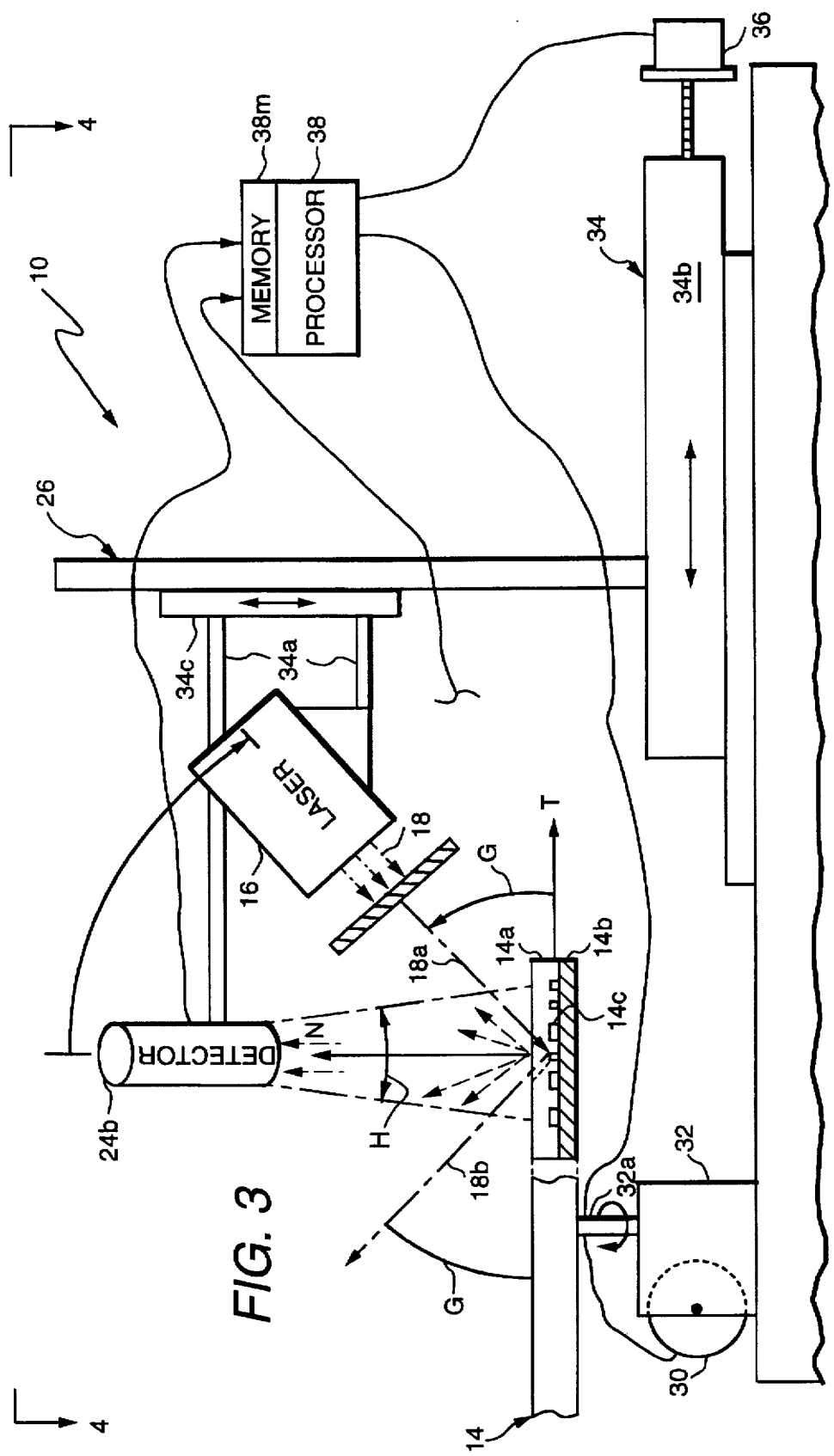
FIG. 3 is an elevational, schematic view of the cloud analyzer illustrated in FIG. 1 in accordance with an exemplary embodiment for scanning a light beam across the optical disc and detecting scattered light therefrom.
Figure 4:
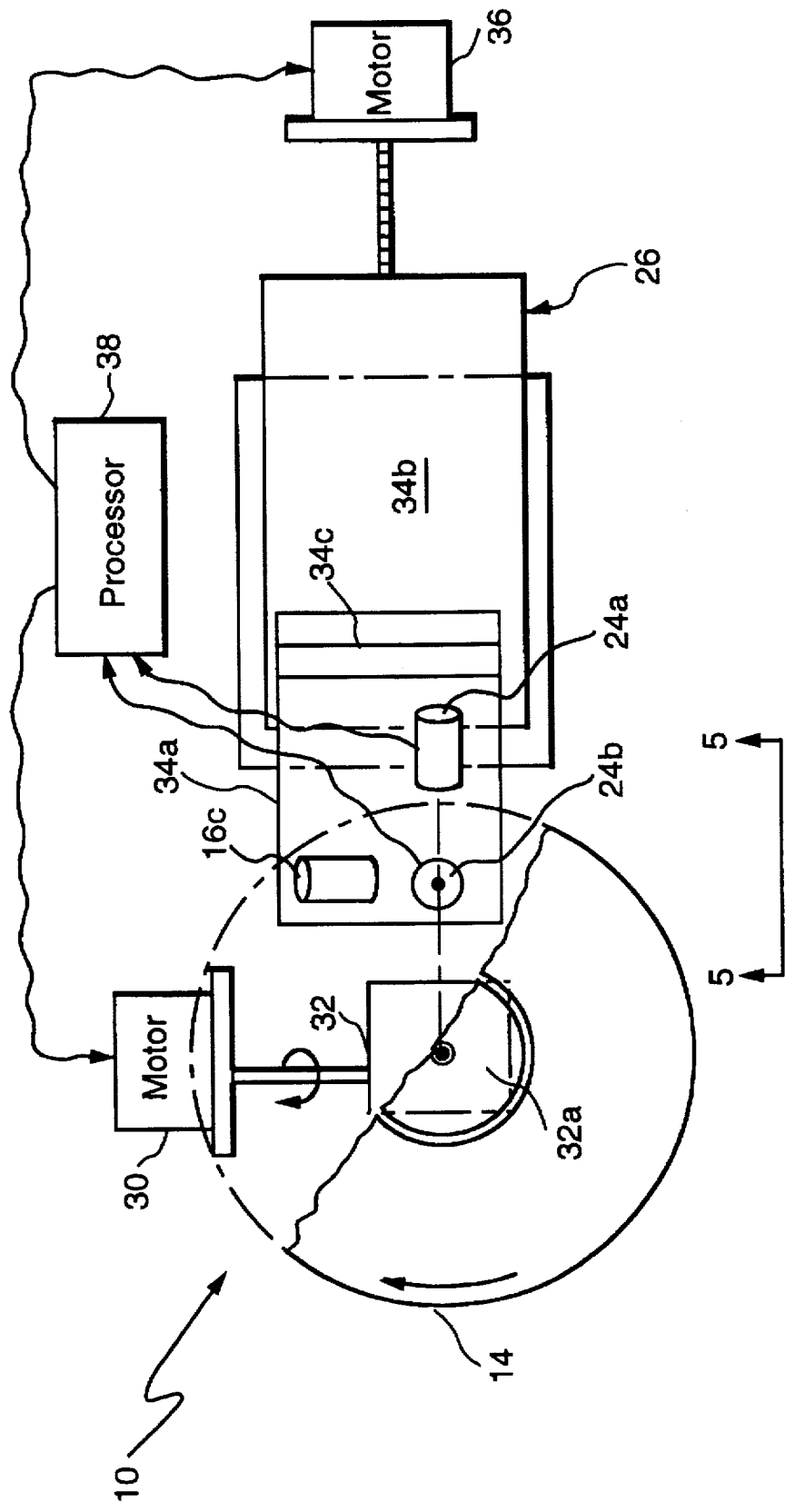
FIG. 4 is a top view of the cloud analyzer illustrated in FIG. 3 and taken along line 4—4.
Figure 5:
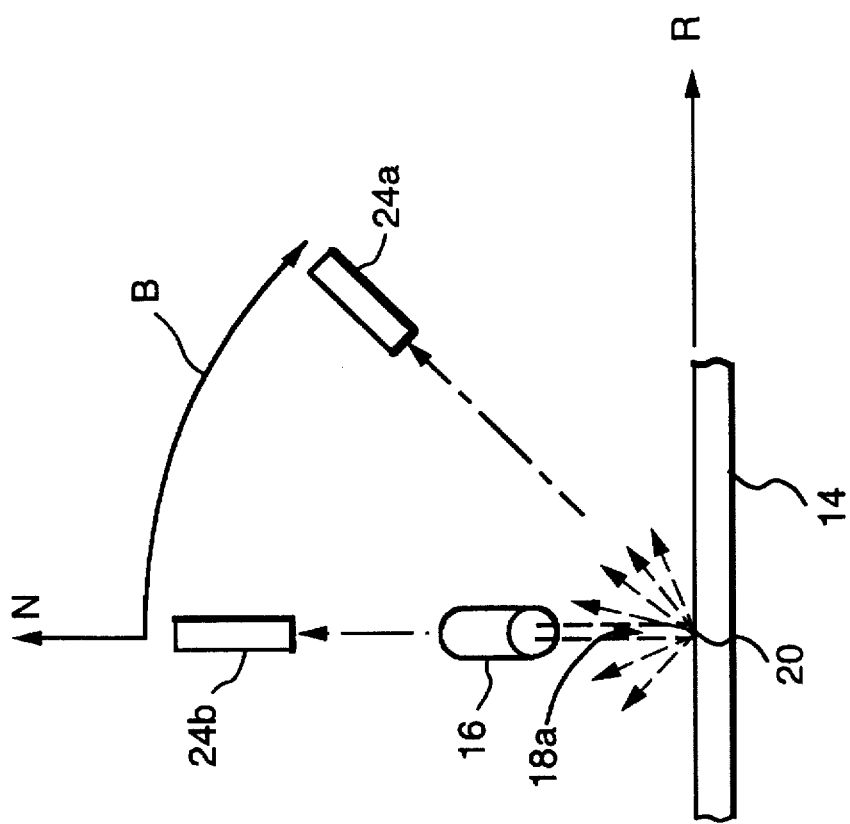
FIG. 5 is a side view of a portion of the cloud analyzer illustrated in FIG. 4 and taken along line 5—5.

FIG. 2 illustrates a flowchart of an exemplary method of detecting scattered light from the optical disc 14 for discerning the cloud 12. FIGS. 3–5 illustrate schematically a preferred embodiment of the cloud analyzer 10 of FIG. 1 for examining the entire surface layer 14a to obtain suitable data points from which the cloud 12 may be detected. As shown in FIGS. 3 and 4, the analyzer 10 includes suitable means in the form of a scanner 26 for suitably scanning the light spot 20 over the surface layer 14a at a plurality of discrete grid locations or positions 28, some of which are illustrated in FIG. 1, with each position 28 covering a plurality of the pits 14c to obtain a plurality of light intensities or data points as the scattered light is detected at each corresponding position 28.

As shown in FIGS. 3 and 4, the scanner 26 preferably includes suitable means in the exemplary form of a first motor 30 operatively joined to a transmission 32 having an output spindle 32a on which is suitably positioned the disc 14 for rotating the disc 14 either continuously or in discrete steps as desired. Suitable means 34 are also provided for concurrently translating the projector 16 and the two detectors 24a,b radially over the optical disc 14 so that in combination with the rotation of the disc 14 the entire surface layer 14a may be examined at a corresponding number of grid positions 28.

The translating means 34 preferably includes a common frame 34a suitably fixedly supporting the projector 16 and both detectors 24a,b in a fixed orientation relative to each other. A horizontally translating ball slide 34b supports the frame 34a, and a second motor 36 is operatively joined to the slide 34b for selectively translating the frame 34a over the disc 14 for positioning the projector 16 and the detectors 24a,b thereover either continuously or in stepwise fashion.

A suitable vertical slide 34c is disposed on the horizontal slide 34b for adjusting vertical position of the frame 34a, and in turn the projector 16 and detectors 24a,b above the disc 14. As shown in FIG. 3, each of the detectors 24a,b has a respective detection cone angle H, and the vertical height of the frame 34a may be suitably adjusted to align the light spot accurately atop the surface layer 14a for maximizing detection efficiency by the detectors 24a,b.

A suitable digitally programmable computer processor or controller 38 is operatively joined to the two motors 30, 36 for controlling their rotary position and in turn controlling the angular position of the disc 14 and the horizontal position of the slide 34b, and in turn the projector and detectors. The processor 38 is also operatively joined to the individual detectors 24a,b for receiving electrical signals therefrom indicative of light intensity. The processor 38 may be in the form of a conventional personal computer for both controlling operation of the analyzer 10 and for performing data analysis and reduction for detecting the cloud 12.

More specifically, by suitably rotating the disc 14 and translating the projector and detectors, the entire surface layer 14a of the disc 14 may be scanned for providing discrete grid positions 28 some of which are illustrated in FIG. 1. For example, 100 concentric annular tracks may be followed, with each track having several hundred discrete positions 28 for providing a complete data grid across the surface layer 14a of suitable density for detecting the cloud 12.

In accordance with another feature of the invention, the processor 38 may be used for data analysis for determining variation or difference of individual ones of the plurality of detected light intensities from a specific reference value of substantially all of the detected light intensities over the entire grid for detecting the cloud 12. Since the cloud 12 is a relative phenomena over the surface of the disc 14, it may be discerned in accordance with the invention by determining the variation of scattered light intensity relative to unclouded regions. The cloud 12 may scatter light to a greater or lesser extent than that scattered by a non-cloud region. By determining the difference between a cloud region and non-cloud regions, the cloud region may be discerned.

Accordingly, the processor 38 as illustrated in FIG. 3 preferably also includes a suitable computer memory 38m for storing the detected light intensities corresponding to the plurality of data points over the entire surface of the disc 14. Each of the two detectors 24a,b separately receives a portion of the scattered light and therefore one set of data points represents the product of the resolution circumferentially and radially for one detector, with another set having the same resolution of data points for the second detector. The two sets of data are suitably stored in the memory 38m, and the processor 38 may be suitably programmed for calculating or determining the standard deviation of the data points to obtain the light intensity variation in the preferred embodiment.

As indicated above, the cloud 12 typically changes in contrast depending upon the direction of the incident beam 18a and the viewing direction represented by the two detectors 24a,b. Accordingly, the directions may be varied and optimized as desired for maximizing the contrast of the cloud 12 relative to the non-cloud regions of the disc 14. Although a single one of the detectors 24a,b may be used, the two detectors 24a,b are preferred for detecting intensity of the scattered light from two different oblique directions from the spot 20 as shown in FIGS. 1 and 5 to increase the contrast of the cloud 12 for improving the detection thereof. As indicated above, the contrast of a cloud varies as a function of the incident light and the viewing direction. By specifically locating the two detectors 24a,b relative to each other and relative to the incident beam 18a, the cloud may be more readily discerned.

In the preferred embodiment illustrated in FIGS. 1 and 3–5, the first detector 24a is preferably positioned generally perpendicular to the incident light beam 18a, and perpendicular to the projector 16, and the second detector 24b is preferably positioned generally perpendicular to the disc surface layer 14a and spaced apart from the first detector 24a.

Spherical coordinates may be used to describe the location of the light source projector 16 and the individual detectors 24a,b relative to the spot 20. FIG. 1 illustrates a spherical coordinate system with three orthogonal axes including a radial axis R, a tangential axis T, and a perpendicular or normal axis N. The location of the projector and detectors may be identified by their radius outwardly from the origin of the coordinate system at the spot 20, and by angular positions from chosen ones of the axes.

For example, the position angle A represents angular orientation in the R-T plane (disc surface) relative to the radial axis R, and the position angle B represents angular orientation relative to the normal axis N. Using these spherical coordinates, the projecting end of the laser 16 is located in one embodiment at a radius of 30 mm from the spot 20, at a position angle A of 90°, and at a position angle B of 45°. This positions the projector 16 coplanar in the N-T plane at 45° to both the tangent axis T and the normal axis N for projecting the light beam 18 toward the spot 20.

The first detector 24a is positioned in one embodiment at a radius of 20 mm from the spot 20 at a position angle A of 0° and a position angle B of 45°. This places the first detector 24a in the R-N plane and equally spaced, at 45°, between the R and N axes. The second detector 24b is also at a radius of 20 mm from the spot 20, and a position angle A of 0° and a position angle B of 0°. This also places the second detector 24b in the R-N plane coaxial with the normal axis N perpendicularly above the spot 20.

The two detectors 24a,b in this preferred embodiment are therefore coplanar with each other in the R-N plane, and equiangularly spaced from both the incident light beam 18a and the specular reflected beam 18b for minimizing the likelihood of detecting these light beams and diffraction orders thereof. Correspondingly, this maximizes the likelihood of detecting scattered light at the spot 20 due to the defects which create the cloud 12. And, by using the two detectors 24a,b spaced apart from each other the ability to detect a cloud is enhanced since multiple viewing angles thereof are provided.

In the preferred embodiment illustrated in FIG. 1 for example, the projector 16 is oriented at a tangent to the circular disc 14 in the vertical N-T plane of the tangent axis T. And, the detectors 24a,b are coplanar along the radial axis R of the disc 14. The scanner 26 illustrated in FIG. 4 accurately positions the two detectors and projector relative to each other and relative to the disc 14.

In order to obtain a suitable array of scattered light intensities over the surface of the disc 14, the disc 14 is suitably rotated by the motor 30, and the detectors and projector are radially translated over the disc 14 using the horizontal slide 34b. This may be accomplished continuously on the fly, or in discrete steps for obtaining discrete data points spaced apart over the surface of the disc 14 with sufficient resolution for detecting the cloud 12.

As shown in FIGS. 4 and 5, the tangentially positioned projector 16 projects the incident light beam 18a on the surface of the disc 14 to position the spot 20 preferably along a radial line of the disc 14. By rotating the disc 14, discrete data points of scattered light concurrently detected by the two detectors 24a,b are obtained along an arcuate track around the circumference of the disc 14. After the disc 14 is rotated one complete turn, the scanner 26 repositions the projector 16 and detectors 24a,b at another radial position, and the disc 14 is again rotated one complete revolution for providing corresponding data points at this radius. The process is continued until a plurality of coaxial, radially spaced apart arcuate tracks are obtained with a suitable number of data points therein for providing sufficient resolution for detecting the cloud 12.

Portions of exemplary arcuate tracks are illustrated schematically in FIG. 1 by the dotted grid positions 28, and in the preferred embodiment, each arcuate track may be an annular or circular ring disposed concentrically about the axial centerline axis of the disc 14. Or the arcuate tracks may be in the form of a continuous spiral from the outer perimeter of the disc 14 to its inner perimeter. Also in the preferred embodiment, the individual grid positions 28 from arcuate track to arcuate track are aligned in a straight line and extend radially outwardly from the center of the disc 14 to define a plurality of circumferentially spaced apart straight radial tracks. In this way the entire top surface of the disc 14 may be examined by the moving spot 20 to develop a suitable, generally uniform grid of data points over the entire surface.

One set or array of data points is obtained for the first detector 24a and a corresponding set or array of data points is obtained for the second detector 24b covering the entire top surface of the disc 14. These data points are suitably stored in the memory 38m and suitable data analysis may then be conducted on the entirety of the data using the processor 38. In particular, the individual data points of detected scattered light intensity may be suitably analyzed for determining differences therebetween for detecting the cloud 12. If no cloud 12 in fact exists and the disc surface layer 14a is uniformly transparent, no differences in scattered light intensity will be detected which indicates a clear disc 14.

However, wherever a specific region of the disc 14 includes a cloud 12 which scatters the light beam 18 with different values than adjacent non-cloud regions, the cloud 12 may then be detected by its constituent parts. A suitable reference coordinate system for the disc 14 is provided for accurately identifying the location of each grid position 28 so that during data reduction a corresponding map of the detected scattered light from the disc 14 may be created and suitably displayed if desired.

In one preferred method, data analysis is separately done for the two sets of data points collected for the two detectors 24a,b. It is desired to determine the statistical standard deviation of the measured scattered light intensity for all of the grid positions along each of the arcuate tracks, which is accomplished by first determining the arithmetic mean value of all of the data points collected for each arcuate track (i.e., the sum of the values of the points divided by the number of points), and then calculating the standard deviation therefor. And then an average standard deviation is calculated for all of the arcuate tracks.

Similarly, it is also preferred to determine the standard deviation of the data points along each of the radial tracks using the arithmetic mean value for each of these tracks. The average standard deviation for all of the radial tracks is then computed. The average track standard deviations for the arcuate and radial tracks are then suitably normalized to provide a single cloud rating or index number representing the degree of clouding in the disc 14.

In one embodiment, the arithmetic mean of the track standard deviations for the arcuate and radial tracks is divided by the arithmetic mean of the scattered light intensities for the entire disc 14 and multiplied by 100 to obtain corresponding coefficients of variation for the collective arcuate tracks and radial tracks, which are two numbers expressed in percent. Corresponding coefficients of variation are obtained separately for the arcuate and radial tracks for each of the two detectors 24a,b providing four values. The arithmetic mean of these four track coefficients of variation is then computed for determining the cloud rating, i.e. the collective sum divided by four.

In tests of the method and apparatus for different CD discs 14, cloud ratings varying from about 4 to about 15 were obtained. Values below about 7 are considered acceptable, with little or no clouding, and values greater than about 7 may be considered unacceptable representing relatively high contrast clouding over a significant surface area of the disc 14.

Accordingly, a single numerical expression of the degree of clouding in an optical disc 14 may now be automatically computed from measured scattered light from the disc 14 for providing a substantial improvement over laborious manual visual inspection. The method and apparatus according to the present invention provides an objective versus subjective evaluation of the disc 14 with consistent and accurately reproducible results.

The analyzer 10 illustrated in the drawings is relatively simple in configuration and function and does not require additional optical devices or lenses for effective operation. The laser 16 provides a suitable collimated light beam 18 which is propagated through the transparent surface layer 14a of the disc 14 to scatter light at the juncture of the various pits 14c due to any clouds found therein. The scattered light is readily detected by simple photodetectors preferably spaced for detecting scattered light with the exclusion of the incident beam 18a and its specular reflection 18b. Although in one embodiment the motors 30 and 36 may be stepping motors controlled by the processor 38 for developing a suitable resolution grid of data points over the entire surface of the disc 14, the method may also be practiced using continuous rotation of the disc 14 and continuous translation of the projector and detectors suitably coordinated for providing a corresponding grid of data points over the disc 14.

Data analysis separately conducted along each of the arcuate data tracks and radial data tracks provides multiple direction analysis relative to each grid position 28 for better discerning any portion of a cloud 12 which might exist at such position. And, by using the two detectors 24a,b suitably spaced apart from each other and relative to the projector 16, additional discrimination in viewing position is obtained for also enhancing contrast of portions of the cloud 12 relative to non-cloud portions for improving performance of the analyzer 10.

The projector 16 and one or more of the detectors 24a,b may be used in alternate embodiments with varying positions thereof for optimizing or maximizing the ability to discern the cloud 12. And, alternate data analysis methods may be used for maximizing the ability to discern the clouds 12 from non-cloud regions based on the measured scattered light intensity. The various data analysis methods may be readily effected in the processor 38 using suitable software specific thereto. And, conventional imaging software may be used in the processor 38 to suitably provide an image map representative of the scattered light intensity over the entire surface of the disc 14 for imaging the cloud 12. The imaging process may use the raw data of scattered light intensity itself or it may use the standard deviation values for the arcuate or radial tracks.

In another embodiment, the analysis may be conducted using a space derivative of the scattered light intensity to determine the rate of change of scattered light between the grid positions. High gradients or derivatives may better discern the boundaries between cloud and non-cloud regions.

What is claimed is:

1. A method of detecting a cloud in an optical disc having a transparent surface layer atop a substrate and data pits therebetween comprising:

projecting a light beam at an acute incidence angle atop said surface layer to define a light spot covering a plurality of said pits;

detecting intensity of light scattered from said pits below said spot obliquely to both said incident light beam and a specular reflection thereof, the detecting intensity further comprising detecting intensity of said scattered light from two different oblique directions from said spot to increase contrast of said cloud;

scanning said light spot over said surface layer at a plurality of discrete positions each covering a plurality of said pits to obtain a plurality of light intensities from said detecting step corresponding to said plurality of positions; and determining variation of individual ones of said plurality of said detected light intensities from a reference value of substantially all of said detected light intensities to detect said cloud.

2. A method according to claim 1 further comprising:

storing said detected light intensities as a corresponding plurality of data points in a computer memory; and determining standard deviation of said data points to obtain said light intensity variation.

3. A method according to claim 1 wherein said two detection directions are substantially coplanar.

4. A method according to claim 1 further comprising:

detecting intensity of said scattered light from a first direction generally perpendicular to said light beam; and detecting intensity of said scattered light from a second direction generally perpendicular to said surface layer.

5. A method according to claim 4 further comprising scanning said light spot over said surface layer to provide a grid thereover of said detected intensities including a plurality of coaxial, radially spaced apart arcuate tracks, and a plurality of straight, circumferentially spaced apart radial tracks.

6. A method according to claim 5 further comprising:

determining an average standard deviation of all of said arcuate tracks;

determining an average standard deviation of all of said radial tracks; and normalizing a sum of said arcuate and radial averages to provide a single cloud rating.

7. An analyzer for detecting a cloud in an optical disc having a transparent surface layer atop a substrate and data pits therebetween comprising:

a projector for projecting a light beam at an acute incident angle atop said surface layer to define a light spot covering a plurality of pits;

at least two detectors for detecting intensity of light scattered from said pits below said spot obliquely to both said incident light beam and a specular reflection thereof from two different oblique directions from said spot to increase contrast of said cloud;

a scanner for scanning said light spot over said surface layer at a plurality of discrete positions each covering a plurality of said pits to obtain a plurality of light intensities corresponding to said plurality of positions; and a processor for determining variation of individual ones of said plurality of detected light intensities from a reference value of substantially all of said detected light intensities to detect said cloud.

8. An analyzer according to claim 7 further comprising:

a memory for storing said detected light intensities as a corresponding plurality of data points; and wherein said processor is configured for determining standard deviation of said data points to obtain said light intensity variation.

9. An analyzer according to claim 7 wherein said two detectors and detection directions are substantially coplanar.

10. An analyzer according to claim 7 wherein said two detectors comprise:

a first detector for detecting intensity of said scattered light from a first direction generally perpendicular to said light beam; and a second detector for detecting intensity of said scattered light from a second direction generally perpendicular to said surface layer.

11. An analyzer according to claim 10 wherein said scanner comprises:

means for rotating said optical disc; and means for concurrently translating said projector and detectors radially over said optical disc.

12. An analyzer according to claim 11 wherein said translating means comprise:

a frame fixedly supporting said projector and detectors in a fixed orientation;

a translating slide supporting said frame; and a motor operatively joined to said slide for selectively translating said slide and frame over said optical disc for positioning said projector and detectors thereove.

13. An analyzer according to claim 12 further comprising means disposed on said slide for adjusting vertical position of said frame above said optical disc.

14. An analyzer according to claim 12 wherein said projector is a laser effective for projecting a collimated laser light beam, and further comprising an aperture optically aligned with said laser for limiting size of said spot.

15. A method of detecting a cloud in an optical disc, the optical disc having a substrate, a transparent surface layer atop the substrate and data pits between the substrate and transparent surface layer, the method comprising:

projecting a light beam at an acute incidence angle atop said surface layer to define a light spot covering a plurality of said pits;

detecting intensity of light scattered from said plurality of said pits below said spot obliquely to both said incident light beam and a specular reflection thereof;

scanning said light spot over said surface layer at a plurality of discrete positions, each discrete position covering a plurality of said pits to obtain a plurality of light intensities corresponding to said plurality of discrete positions;

determining variation of individual ones of said plurality of said light intensities from a reference value of substantially all of said detected light intensities thus detecting the cloud in the optical disc; and further comprising detecting intensity of said scattered light from at least two different oblique directions from said spot to increase contrast of the cloud in the optical disc.

16. A method according to claim 15, further comprising:

storing said detected light intensities as a corresponding plurality of data points; and determining standard deviation of said data points to obtain said light intensity variation.

17. A method according to claim 15, wherein said two detection directions are substantially coplanar.

18. A method according to claim 15, wherein the detecting further comprises:

detecting intensity of said scattered light from a first direction generally perpendicular to said light beam; and detecting intensity of said scattered light from a second direction generally perpendicular to said surface layer.

19. A method according to claim 15, further comprising: scanning said light spot over said surface layer to provide a grid of said detected intensities, the grid including a plurality of coaxial, radially spaced apart arcuate tracks, and a plurality of straight, circumferentially spaced apart radial tracks.

20. A method according to claim 19, further comprising:

determining an average standard deviation of all of said arcuate tracks;

determining an average standard deviation of all of said radial tracks; and normalizing a sum of said arcuate and radial averages to provide a single cloud rating.

21. An analyzer for detecting a cloud in an optical disc, the optical disc having a substrate, a transparent surface layer atop the substrate and data pits between the substrate and the transparent layer, the analyzer comprising:

a projector that projects at least one light beam at an acute incident angle atop said surface layer to define at least one light spot covering a plurality of pits;

at least one detector that detects intensity of light scattered from said pits below said spot obliquely to both an incident light beam and a specular reflection thereof;

a scanner that scans said light spot over said surface layer at a plurality of discrete positions each covering a plurality of said pits to obtain a plurality of light intensities corresponding to said plurality of positions;

a processor that determines variation of individual ones of said plurality of detected light intensities from a reference value of substantially all of said detected light intensities wherein the determination of variation detects the cloud; and further comprising two of said detectors for detecting intensity of said scattered light from two different oblique directions from said spot to increase contrast of said cloud.

22. An analyzer according to claim 21, further comprising:

a memory that stores said detected light intensities as a corresponding plurality of data points; and wherein said processor is configured for determining standard deviation of said data points to obtain said light intensity variation.

23. An analyzer according to claim 21, wherein said two detectors and detection directions are substantially coplanar.

24. An analyzer according to claim 21, wherein said two detectors comprise:

a first detector for detecting intensity of said scattered light from a first direction generally perpendicular to said light beam; and a second detector for detecting intensity of said scattered light from a second direction generally perpendicular to said surface layer.

25. An analyzer according to claim 21, wherein said scanner comprises:

means for rotating said optical disc; and means for concurrently translating said projector and detectors radially over said optical disc.

26. An analyzer according to claim 25, wherein said translating means comprise:

a frame fixedly supporting said projector and detectors in a fixed orientation;

a translating slide supporting said frame; and a motor operatively joined to said slide for selectively translating said slide and frame over said optical disc for positioning said projector and detectors thereover.

27. An analyzer according to claim 25, further comprising means disposed on said slide for adjusting vertical position of said frame above said optical disc.

28. An analyzer according to claim 21, wherein said projector is a laser effective for projecting a collimated laser light beam, and further comprising an aperture optically aligned with said laser for limiting size of said spot.

* * * * *